(12) United States Patent
Freidel

(10) Patent No.: US 6,374,044 B1
(45) Date of Patent: Apr. 16, 2002

(54) VEHICLE VAPORIZER

(76) Inventor: Alan Freidel, 7231 SW. 146th Ter., Miami, FL (US) 33158

( * ) Notice: Subject to any disclaimer, the term of this patent is extended or adjusted under 35 U.S.C. 154(b) by 0 days.

(21) Appl. No.: 09/629,388

(22) Filed: Aug. 1, 2000

(51) Int. Cl.7 .................................................. F24F 6/00
(52) U.S. Cl. ............................ 392/390; 239/34; 239/50; 261/140; 261/141
(58) Field of Search .................................. 392/390, 391, 392/392, 394, 395; 239/34, 50, 54, 55, 56, 57; 261/140, 142, DIG. 65

(56) References Cited

U.S. PATENT DOCUMENTS

| | | | | |
|---|---|---|---|---|
| 4,391,781 A | * | 7/1983 | van Lit ........................ | 392/395 |
| 4,523,870 A | * | 6/1985 | Spector ........................ | 239/55 |
| 4,849,606 A | * | 7/1989 | Martens, III et al. ........ | 392/395 |
| 5,373,581 A | * | 12/1994 | Smith .......................... | 392/395 |
| 5,394,506 A | * | 2/1995 | Stein et al. .................. | 392/395 |
| 5,695,692 A | * | 12/1997 | Kennedy ...................... | 239/55 |
| 6,078,728 A | * | 6/2000 | O'Rourke et al. ........... | 392/390 |
| 6,154,607 A | * | 11/2000 | Flashinski et al. .......... | 392/390 |

* cited by examiner

*Primary Examiner*—Sang Paik
(74) *Attorney, Agent, or Firm*—Baker Botts L.L.P.

(57) ABSTRACT

A vehicle vaporizer includes an elongated case having a plug at its distal end, the plug being adapted to be received in the socket of a vehicle cigarette lighter, and a tray receptacle in its proximal end, the tray receptacle having an opening at the proximal end of the case. A tray received in the tray receptacle for movement axially of the case is adapted to support a porous pad impregnated with a vaporizable substance and is movable out of the tray receptacle through the opening for manual replacement of a pad on the tray and into the tray receptacle for operation. An electrical resistance heating element is electrically connected to terminals on the plug for energization by the vehicle cigarette lighter and is positioned in the case adjacent the tray receptacle. Ventilation openings in portions of the case on opposite sides of the tray receptacle and in the tray enable conduction of a thermally induced flow of ambient air through a pad received on the tray by the heating element so as to transport vapor from the pad into the vehicle.

10 Claims, 3 Drawing Sheets

VEHICLE VAPORIZER

BACKGROUND OF THE INVENTION

Juvenile Products Corp. of Miami, Fla. ("Juvenile"), which holds license rights in the present invention, markets a waterless vaporizer, which is described and shown in U.S. Pat. No. 5,970,212 (Freidel, Oct. 19, 1999) for "Waterless Vaporizer," (hereby incorporated by reference for all purposes). The Juvenile vaporizer has a small electrical resistor that thermally induces an air flow through openings in the case and through a refill pad supported on a pad-supporting grille on the top of the case. The pad is impregnated with a vaporizable substance, such as menthol dissolved in eucalyptus oil, and the thermally induced air flow vaporizes the substance and conducts the vapor into the environment. The Juvenile vaporizer described above is configured and constructed for use in a room of a building and is energized by ordinary household current.

Closed vehicles, such as cars, vans, utility vehicles, trucks, boats with closed cabins, and the like, present an environment for their occupants that in some circumstances can be unpleasant. For example, even with a good ventilating system a closed road vehicle driven in heavy traffic or in an area with significant air pollution can become stuffy and malodorous. Many individuals, moreover, are used to aroma therapy in a room setting and would benefit from having aroma therapy readily available in a vehicle. Vehicle occupants are also prone to drowsiness, which is, of course, very undesirable and dangerous in the case of the driver.

SUMMARY OF THE INVENTION

An object of the present invention is to provide a vaporizer that is configured and constructed to be used in a vehicle, especially a land motor vehicle of a personal-use type (as distinguished from, for example, a mass transit vehicle). A further object is to provide a vaporizer that is capable of use with various substances that serve various purposes, such as providing aroma therapy, air-freshening, and inhibiting drowsiness.

The foregoing objects are attained, in accordance with the present invention, by a vehicle vaporizer that includes an elongated case having a plug at its distal end, the plug being adapted to be received in the socket of a vehicle cigarette lighter, and a tray receptacle in its proximal end, the tray receptacle having an opening at the proximal end of the case. A tray is received in the tray receptacle for movement axially of the case, is adapted to support a porous pad impregnated with a vaporizable substance, and is movable out of the tray receptacle through the opening for manual replacement of a pad on the tray and into the tray receptacle for operation. An electrical resistance heating element is electrically connected to terminals on the plug for energization by the vehicle cigarette lighter and is positioned in the case adjacent the tray receptacle. Ventilation openings in portions of the case on opposite sides of the tray receptacle and in the tray enable conduction of a thermally induced flow of ambient air through a pad received on the tray by the heating element so as to transport vapor into the vehicle.

A vehicle vaporizer, according to the present invention, is of simple construction, can be produced at a low cost, is small in size, and is extremely easy to use. The user need only pull the tray out of the case, place a pad on the tray, push the tray back into the case, and insert the vaporizer into the cigarette lighter of the vehicle. A very small amount of heat generated by the energized heating element is sufficient to induce a flow of ambient air through the case and the pad and carry vapor from the pad into the vehicle. The vaporizer is completely safe to use. In that regard, the outside surface of the case is heated to only about 100 degrees F. when the vaporizer is in use. Power consumption is very low—only about two watts is adequate to produce the air flow needed to cause emission of vapor into the vehicle. The vaporizer can be used with pads impregnated with a variety of substances, such as menthol and eucalyptus oil for respiratory relief, peppermint oil for alertness, or a wide variety of other purpose-driven aromatherapy oils, as selected by the user.

In preferred embodiments, the tray is movable along the tray receptacle to a plurality of axial positions so as to vary the degree of exposure of a pad received on the tray to the thermally induced flow of air produced by the heating element. This feature allows the user to choose the intensity of the vapor in the vehicle. For convenience of adjustment, the case has a slot along each side of the tray receptacle, and the tray includes a manually engageable lug protruding through each slot and projecting from the case for facilitating movement of the tray along the tray receptacle. The case and the tray, preferably, have coacting detents arranged to maintain the tray in each of the plurality of positions. It is desirable for the tray to be received fully within the case in all of the plurality of positions.

The case and the tray may have coacting stop surfaces arranged to prevent the tray from being separated from the case when the case is moved out of the tray receptacle for replacement of a pad. The stop surfaces may, for example, be the ends of the slots in the case and the edges of the protruding lugs.

It is advantageous to construct the tray to have a bottom wall, end walls and side walls so as to support a pad on the ends and sides. The side walls may be joined solely to the proximal end wall of the tray so as to form deflectable arms, each of which includes a manually engageable lug adjacent the distal end (the end remote from the proximal end wall of the tray). In that arrangement, the case has a slot in each side of the tray receptacle, one for each lug, and the side walls of the tray and the case have coacting detents arranged adjacent the lugs to maintain the tray in each of the plurality of positions.

DESCRIPTION OF THE DRAWINGS

For a more complete understanding of the present invention, and the advantages thereof, reference may be made to the following written description of an exemplary embodiment, taken in conjunction with the accompanying drawings.

8—top plan;

9—left side elevational;

10—proximal end elevational; and

11—distal end elevational; and

Figure 12:
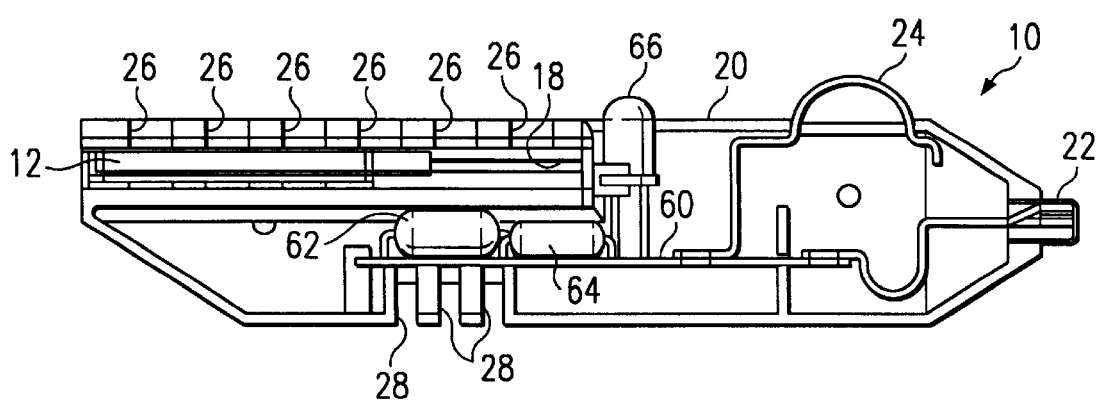
Figure 3:
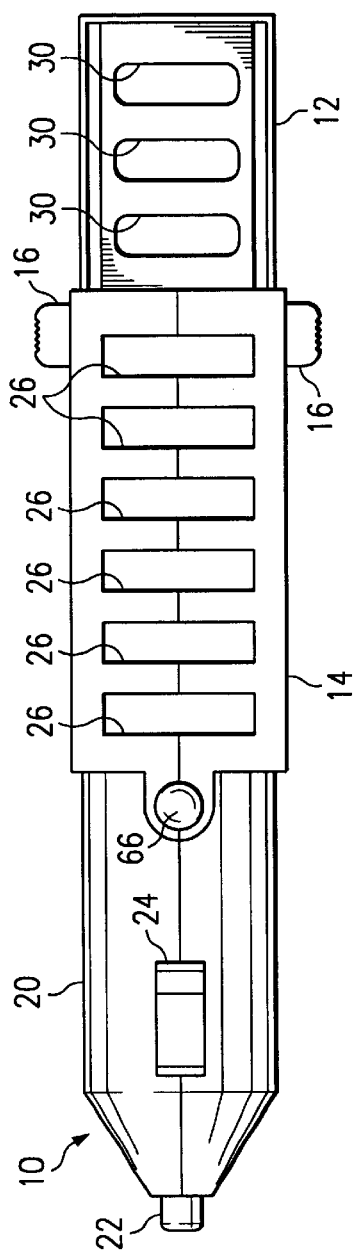
FIG. 3 is top plan view of the embodiment, showing the drawer open.
Figure 4:
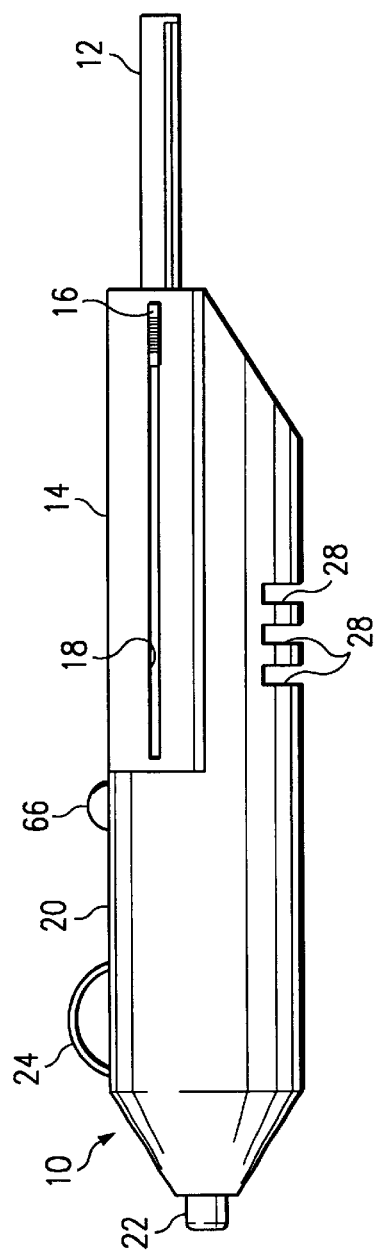
FIG. 4 is a left side elevational view, showing the drawer open and is also a substantially a mirror image of the right side.
Figure 5:
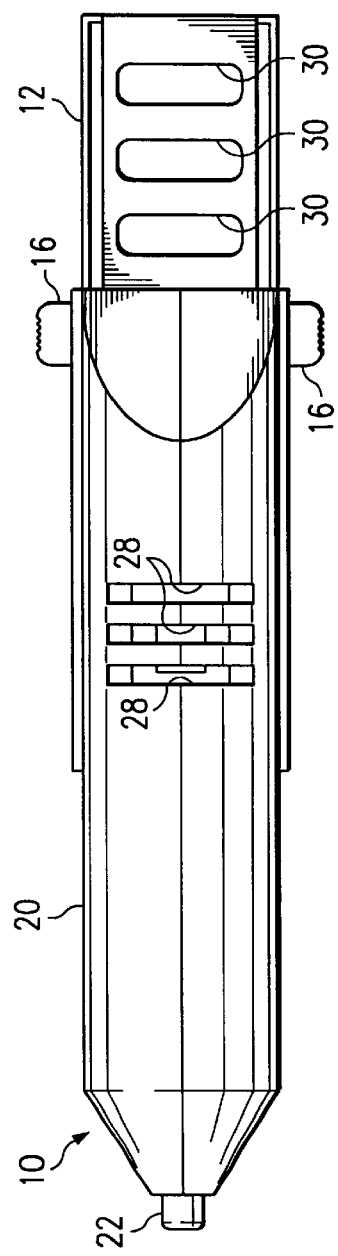
FIG. 5 is a bottom plan view, showing the drawer open.
Figure 6:
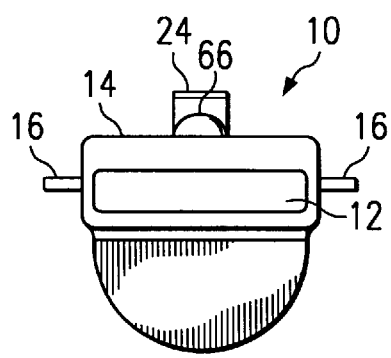
FIG. 6 is an elevational view of the proximal end.
Figure 7:
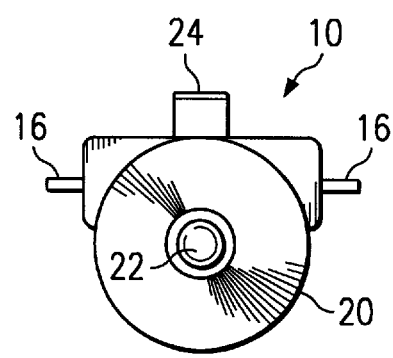
FIG. 7 is an elevational view of the distal end.
Figure 8:
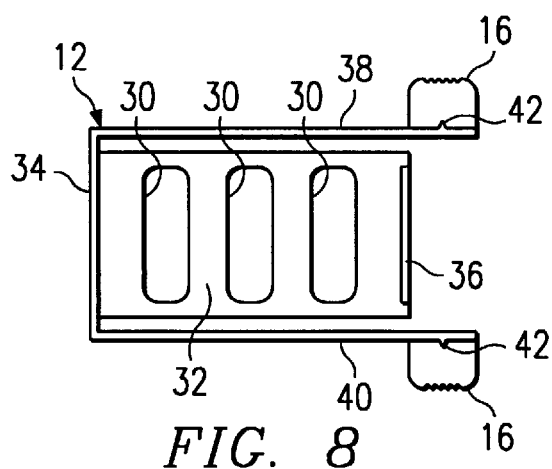
FIGS. 8 to 11 are views of the drawer, as follows.
Figure 9:
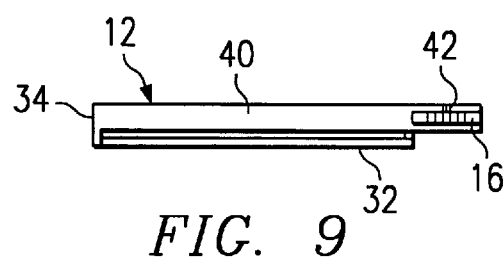
Figure 10:
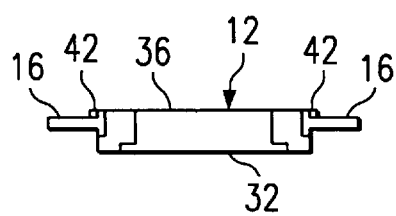
Figure 11:
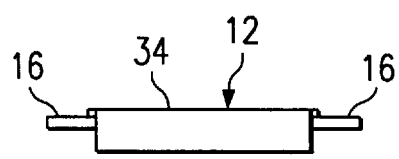

FIG. 12 is a right side elevational view of the embodiment, showing it with the right side of the case removed.

DESCRIPTION OF THE EMBODIMENT

Figure 1:
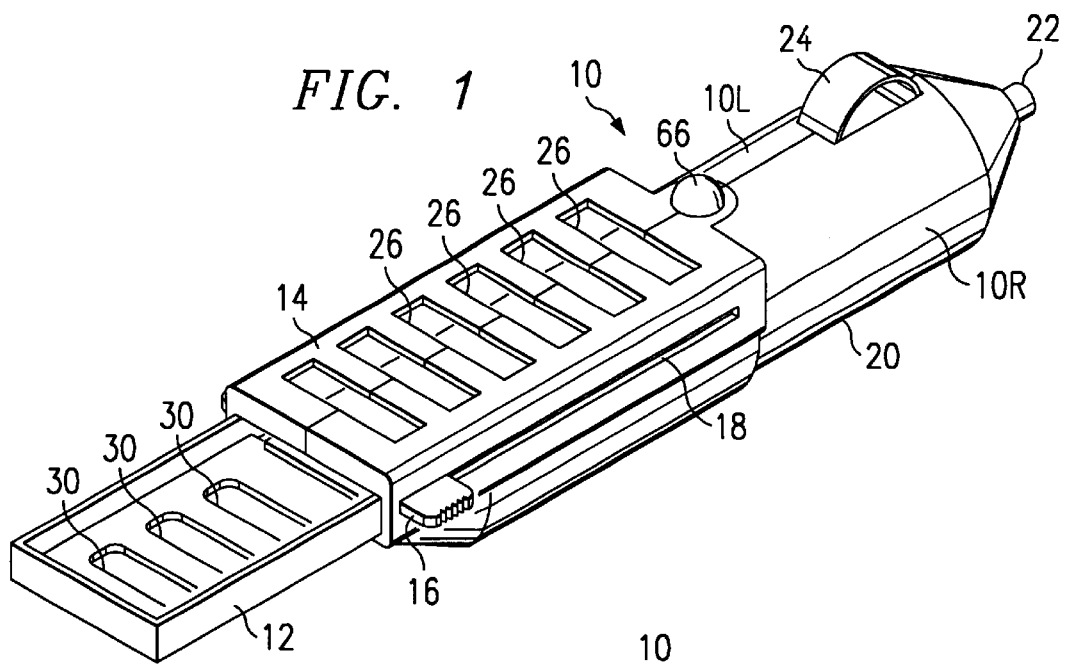
FIG. 1 is a three-quarter top perspective view of the embodiment, showing it with the drawer for the pad open.
Figure 2:
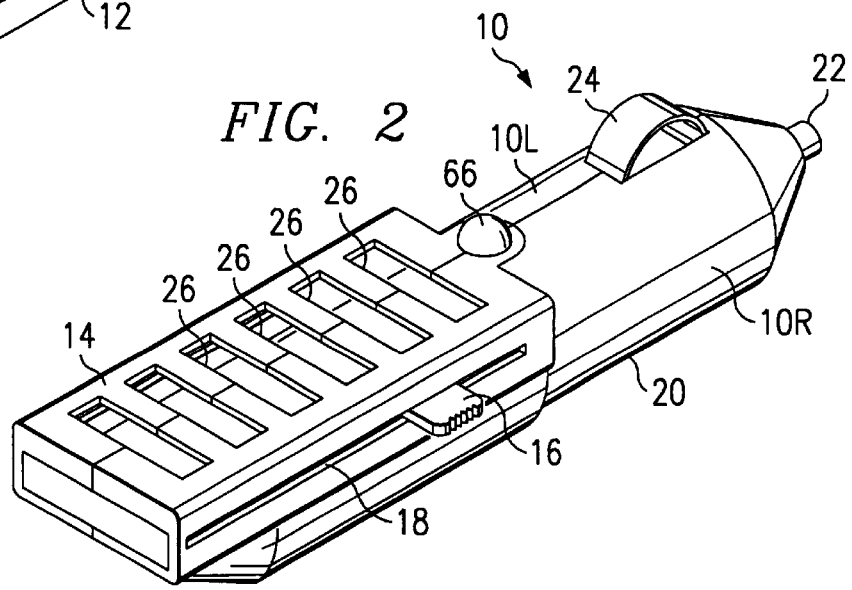
FIG. 2 is a three-quarter top perspective view of the embodiment, showing it with the drawer for the pad closed.

The embodiment of a vehicle vaporizer shown in the drawings has a hollow, elongated case 10 and a tray 12 that is slidably received in a tray receptacle 14 at the proximal end of the case so as to be movable axially of the case between an open position, in which most of it extends out from the proximal end of the case (FIG. 1) to facilitate placing a porous pad impregnated with a vaporizable substance on the tray, and a closed or fully inserted position (FIG. 2), in which it is fully received in the case and the pad on the tray is captured within the case. Lugs 16 on the sides of the tray 12 extend out of the case through slots 18 along the sides of the tray receptacle 14 and are manually engaged to move the tray axially of the case to a selected position, as described below.

The distal end portion of the case is a plug 20, which is of a size and shape that enables it to be inserted into the cigarette lighter receptacle of a vehicle. A positive electrical contact 22 and a negative electrical contact 24 on the plug 20 connect the positive and negative contacts of the vehicle cigarette lighter receptacle to energize an electrical resistance heating element (see below) received within the case 10. Heat from the heating element thermally induces a flow of ambient air through holes 26 and 28 in the top and bottom walls the case adjacent the tray receptacle 14 and holes 30 in the tray 12. The air flow transports vapor from the pad into the vehicle interior.

The tray 12 (see FIGS. 8 to 11) has a bottom wall 32, a proximal end wall 34 to which the proximal end of the bottom wall is attached, a distal end wall 36 attached to the distal end of the bottom wall, and a pair of side walls 38 and 40. The side walls 38 and 40 are attached solely to the side edges of the proximal end wall so as to make them resiliently deflectable arms. The lugs 16 extend out from the free, distal ends of the side walls 38, 40, and are located distally of the distal end wall 36 of the tray. Thus, when the proximal edges of the lugs 16 engage the proximal ends of the slots 18 in the sides of the case 10, the lugs and slots act as stops and keep the tray from being detached from the case. Also, the location of the lugs distally of the distal end of the tray allows the tray proper to be extended fully out of the case to enable a pad to be placed on it. Small projections 42 on the side walls 38, 40 form one element of a detent for holding the tray 12 in each of three selected positions axially of the case 10.

The case 10 consists of two injection-molded parts 10R and 10L, which are joined by screws (not shown). The design of the parts of the case is a matter of routine skill. Therefore, the parts are not described or shown in detail. Each part has internal ribs that form slideways for the upper and lower edges of the side walls 38 and 40 of the tray 12—the distal part of the tray is also supported and guided by the lugs 16—and for supporting a circuit board 60 on which the electrical parts of the vaporizer are mounted. The inner portion of the upper edge of each slot 18 in each part of the case 10 has three axially spaced-apart notches (not shown) that form the other elements of the detents and accept the projections 42.

The details of the circuit board are not shown. The electrical system, the elements of which are shown in FIG. 12, consists of an electrical resistor 62 connected between the contacts 22 and 24 that serves as an electrical heating element—note that the contacts are configured and mounted to be resilient—and an LED 66 that is connected in series with an electrical resistor 64 between the contacts 22 and 24 in parallel with the resistor 62. The LED serves, of course, as an indicator light that lights up when the vaporizer is in operation.

FIG. 12 shows the tray 12 in a position that provides a "low" output of vapor. The tray is located at the proximal end of the receptacle 14 and proximally of the resistor 62, where very little of the thermally-induced flow of air passes through it. The heating resistor 62 is positioned nearer the distal end of the tray receptacle 14 of the case. A "medium" vapor output position of the tray is located distally of the position shown in FIG. 12, where the lugs 16 are about midway between the illustrated position and the distal ends of the slots 18. The maximum vapor output is provided when the tray is located in the "high" position, in which the lugs 16 are at the distal ends of the slots 18 and the pad on the tray is located directly above the resistor 62. As mentioned above the low, medium, and high positions are set by detents (42) between the tray 12 and the case 10. The user moves the tray between the positions by manipulating the lugs 16.

What is claimed is:

1. A vehicle vaporizer comprising an elongated case having a plug at its distal end, the plug being adapted to be received in the socket of a vehicle cigarette lighter, and a tray receptacle in its proximal end, the tray receptacle having an opening at the proximal end of the case;

an electrical resistance heating element electrically connected to terminals on the plug for energization by the vehicle cigarette lighter and positioned in the case adjacent the tray receptacle;

a tray received in the tray receptacle for movement axially of the case, adapted to support a porous pad impregnated with a vaporizable substance, and movable out of the tray receptacle through the opening for manual replacement of a pad on the tray and into the tray receptacle for operation, and the tray being movable manually by a user along the tray receptacle to a plurality of axial positions so as to vary the degree of exposure of a pad received on the tray to a thermally induced flow of air produced by the heating element;

the case including a slot adjacent a side of the tray receptacle and the tray including a manually engageable lug protruding through the slot and projecting from the case for facilitating manual movement of the tray by the user along the tray receptacle; and ventilation openings in portions of the case on opposite sides of the tray receptacle and in the tray for conduction of the thermally-induced flow of ambient air through the pad.

2. The vehicle vaporizer according to claim 1 wherein the case and the tray have coacting detents arranged to maintain the tray in each of the plurality of positions.

3. The vehicle vaporizer according to claim 1 wherein the tray is received fully within the case in all of the plurality of positions.

4. The vehicle vaporizer according to claim 1 wherein the tray is received fully within the case in all of the plurality of positions.

5. The vehicle vaporizer according to claim 1 wherein the tray has a bottom wall, end walls and side walls, the side walls are attached solely to one end wall so as to form defectable arms, the case includes a slot adjacent each side wall of the tray, and each side wall of the tray includes a manually engageable lug adjacent the end remote from the one end wall protruding through the slot and projecting from the case for manual engagement to facilitate movement of the tray along the tray receptacle.

6. The vehicle vaporizer according to claim 5 wherein the side walls of the tray and the case have coacting detents arranged to maintain the tray in each of the plurality of positions.

7. The vehicle vaporizer according to claim 5 wherein each slot and each lug have coating stop surfaces arranged to prevent the tray from being separated from the case when the case is moved out of the tray receptacle for replacement of a pad.

8. The vehicle vaporizer according to claim 5 wherein the tray is received fully within the case in all of the plurality of positions.

9. A vehicle vaporizer comprising an elongated case having a plug at its distal end, the plug being adapted to be received in the socket of a vehicle cigarette lighter, and a tray receptacle in its proximal end, the tray receptacle having an opening at the proximal end of the case;

an electrical resistance heating element electrically connected to terminals on the plug for energization by the vehicle cigarette lighter and positioned in the case adjacent the tray receptacle;

a tray received in the tray receptacle for movement axially of the case, adapted to support a porous pad impregnated with a vaporizable substance, and movable out of the tray receptacle through the opening for manual replacement of a pad on the tray and into the tray receptacle for operation, and the tray being movable manually by a user along the tray receptacle to a plurality of axial positions so as to vary the degree of exposure of a pad received on the tray to a thermally induced flow of air produced by the heating element;

ventilation openings in portions of the case on opposite sides of the tray receptacle and in the tray for conduction of the thermally-induced flow of ambient air through the pad; and the case and the tray having coacting stop surfaces arranged to prevent the tray from being separated from the case when the case is moved out of the tray receptacle for replacement of a pad.

10. The vehicle vaporizer according to claim 9 wherein the case includes a slot adjacent a side of the tray receptacle and the tray includes a manually engageable lug protruding through the slot and projecting from the case for facilitating manual movement of the tray along the tray receptacle by the user and wherein the slot and the lug have coating stop surfaces arranged to prevent the tray from being separated from the case when the case is moved out of the tray receptacle for replacement of a pad.

* * * * *